(12) United States Patent
Sherratt et al.

(10) Patent No.: US 6,423,349 B1
(45) Date of Patent: Jul. 23, 2002

(54) THERAPEUTIC NUTRIENT COMPOSITION FOR PRE AND POST ELECTIVE SURGERY

(75) Inventors: J. Dale Sherratt, Sherborn; Joann Somerville, Reading, both of MA (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/644,544

(22) Filed: Aug. 24, 2000

(51) Int. Cl.$^7$ .................. A61K 31/07; A61K 31/195; A61K 31/355; A61K 31/375; A61K 31/4985

(52) U.S. Cl. .................. 424/630; 426/72; 426/73; 426/74; 424/439; 424/632; 424/633; 424/634; 424/635; 424/637; 424/638; 424/641; 424/643; 424/681; 424/682; 424/683; 424/686; 424/688; 424/689; 424/692; 424/697; 424/702; 514/249; 514/458; 514/474; 514/494; 514/499; 514/500; 514/561; 514/562; 514/563; 514/706; 514/725; 514/904; 514/905

(58) Field of Search .................. 514/561–563, 514/725, 474, 458, 249, 494, 706, 499, 500, 904, 905; 426/72, 73, 74; 424/630, 632–635, 637, 638, 641, 643, 681–683, 686, 688, 689, 692, 697, 702, 439

(56) References Cited

U.S. PATENT DOCUMENTS

| | | | |
|---|---|---|---|
| 5,292,722 A | 3/1994 | Wilmore | 514/23 |
| 5,646,187 A | 7/1997 | Vinnars et al. | 514/557 |
| 5,902,829 A | 5/1999 | Schneider et al. | 514/565 |
| 6,051,260 A * | 4/2000 | Liska et al. | 424/602 |

FOREIGN PATENT DOCUMENTS

| | | | |
|---|---|---|---|
| EP | 0891719 | * | 1/1999 |
| WO | 00/53176 | * | 9/2000 |
| WO | 01/26642 | * | 4/2001 |

OTHER PUBLICATIONS

C. James Carrico, M.D. et al. "Multiple–Organ–Failure Syndrome" ARCH SURG—vol. 121, pp. 196–197, (Feb. 1986) Published by the American Medical Association.

Guillermo Gutierrez et al. "Gastric intramucosal pH as a therapeutic index of tissue oxygenation in critically ill patients" The Lancet vol. 339 No. 8787, pp. 195–199 (Saturday Jan. 25, 1992) Published by Williams & Wilkins.

Ernest E. Moore, M.D. "Trauma Systems, Trauma Centers, and Trauma Surgeons: Opportunity in Managed Competition" The Journal of Trauma: Injury, Infection, and Critical Care vol. 39, No. 1, pp. 1–11 (1995) Published by Williams & Wilkins.

Orlando C. Kirton, et al. "Failure of Splanchnic Resuscitation in the Acutely Injured Trauma, Patient Correlates with Multiple Organ System Failure and Death in the Intensive Care Unit" CHEST vol. 108, No. 3, p. 104S (Sep. 1995) Published by American College of Chest Physicians.

Orlando C. Kirton, et al. "Persistent Un–Corrected Intramucosal pH (pH1) In The Critically Injured: The Impact of Splanchnic and Antioxidant Therapy" The Journal of Trauma: Injury, Infection, and Critical Care vol. 39, No. 6, p. 1211 (Dec. 1995) Published by Williams & Wilkins.

* cited by examiner

Primary Examiner—John Pak
(74) Attorney, Agent, or Firm—Jeffrey C. Nichols; Mark J. Buonaiuto; Francis C. Kowalik

(57) ABSTRACT

Compositions comprising glutamine in combination with other nutrients, including N-acetyl-cysteine and Vitamins A, C, E are disclosed. Such compositions can be administered for promoting recovery in patients undergoing elective surgery and for treating multiple organ system failure.

43 Claims, No Drawings

THERAPEUTIC NUTRIENT COMPOSITION FOR PRE AND POST ELECTIVE SURGERY

BACKGROUND OF THE INVENTION

1. Field of the Invention

The present invention relates to the use of the amino acid glutamine in combination with additional nutrients in a composition for promoting recovery in patients undergoing elective surgery and for treating multiple organ system failure.

2. Description of the Related Art

Schneider et al., U.S. Pat. No. 5,902,829, discloses a method for the amelioration of microcirculatory hypoperfusion, and/or the treatment or prophylaxis or hypoperfusion-reperfusion injury, in patients in need of such amelioration, treatment or prophylaxis, comprising administering preoperatively to a patient undergoing surgery to the patient a composition comprising an effective amount of a nitric oxide donor and/or a substrate of nitric oxide synthetase and/or a precursor of the substrate, for the amelioration, treatment or prophylaxis, and a nutritionally acceptable carrier. Schneider et al. further discloses that the precursor of L-arginine is ornithine or glutamine and that the composition is administered at least one day prior to surgery, but can be initiated between 3–10 days prior to surgery.

Vinnars et al., U.S. Pat. No. 5,646,187, discloses a composition for the treatment of critically ill patients having one or more organ failures or sepsis and a general catabolism which have more than a 50% reduction of the glutamine level in skeletal muscles and under intensive care, in order to improve protein synthesis capacity, maintaining energy level, preserving the lean body mass, wherein the composition consists essentially of a conventional amino acid mixture and more than 25 gl of alpha-ketoglutarate or admixtures of these with at least one member selected from the group consisting of glutamine, L-asparagine, acetoacetate, glucose and fat.

Wilmore, U.S. Pat. No. 5,292,722, discloses a composition for decreasing dehydration and nitrogen loss in a mammal comprising from about 4% to 10% dextrose and from about ½% to 2% glutamine, or glutamine equivalent, wherein said glutamine equivalent is capable of being converted to glutamine by said mammal. Wilmore discloses that the composition can be used in treating dehydration and nitrogen loss which is associated with surgical operations.

3. Discussion of the Background of the Invention

Throughout the world, multiple organ system failure (MOSF) has become the most common cause of death in intensive care units (ICU); the reported mortality rates vary from 30–100% with a mean of 50%, depending on the number of organ systems involved, the patients' ICU stay may last for 6 weeks to many months. As used herein, the term "MOSF or Multiple Organ System Failure" refers to the clinical syndrome of vital organ dysfunction or failure due to tissue injury resulting from SIRS (Systemic Inflammatory Response Syndrome which refers to the excessive and dysfunctional elaboration by a human patient of inflammatory mediators which results in an excessive and injurious inflammatory response). In prior studies, patients with multiple system failure have used nearly 40% of the available ICU days. See, e.g., Carrico et al. Arch. Surg. Vol. 121 page 196(1986). For the last ten years, efforts to improve outcome based upon increasing systemic oxygen delivery have been advocated, but either no effect or increased mortality has been associated with this approach.

Gastric intramucosal pH monitoring has been advocated as a more sensitive endpoint of resuscitation and two clinical studies have suggested improved outcome in selected subsets of patients. See Gutierrez et al., Lancet, vol. 339 page 195 (1992) and Ivatury et al., J. Trauma vol. 39, page 1, (1995). Others have confirmed that failure of splanchnic resuscitation correlates with MOSF and increased length of ICU stay in a hemodynamically unstable trauma patient. See, e.g., Kirton et al., Chest, vol. 108, No. 3, page 104S (1995).

Kirton et al. have studied ICU patients with persistent uncorrected gastric intramucosal pH and who had pulmonary artery catheters to guide resuscitation. See Kirton et al., J. Trauma vol. 39, No. 6, page 1211(1995). Kirton et al. have found that the relative risk of death in patients with a $pH_i$ of less than 7.32 was 4.5 whereas the relative risk of developing multiple organ system failure was 5.4 in patients having a $pH_i$ of greater than 7.32. During the study a resuscitation protocol was begun upon ICU admission, which utilized inotropic and vasodilatory agents to optimize systemic and splanchnic $O_2$ delivery (e.g., dubutamine, isoproterenol, prostaglandin E, nitroglycerin, nitroprusside). The xanthine oxidase inhibitor, folate, and the free radical scavenger, mannitol, were uniformly administered. Drugs causing splanchnic vasoconstriction (e.g., epinephrine, norephinephrine, meosynephrine) were only used to treat severe systemic hypotension. This protocol resulted in a significant reduction in multiple organ system failures per patient and length of ICU and total hospital stay in patients with persistent gastric intramucosal acidosis. The agents administered increased splanchnic perfusion and were intended to prevent free radical damage during reperfusion. The study concluded that the severity of MOSF as judged by defined organ system failures and duration of stay were associated with gastrointestinal intramucosal acidosis related to splanchnic hypoperfusion. However, the problem of reversing the abnormal $pH_i$ and curtailing the long ICU stay indicated that further improvements are necessary.

Multiple organ system failure is associated with ischemia-reperfusion injury. Oxygen radicals are involved during ischemia followed by reperfusion. Therapy to block xanthine oxidase and thus prevent the generation of free radicals (e.g., superoxicde:$O_2$, hydrogen peroxide:$H_2O_2$, and the hydroxyl radical:OH) and promote the generation of radical scavengers to prevent damage when radicals have already been generated are essential to treatment of multiple organ system failure. The oxygen free radicals are capable of causing cellular injury through cellular membrane lipid peroxidation and degradation of nucleic acids, eventually leading to increased membrane permeability and cell-lysis. Certain free radical species, including $O_2$—and OH cause polymorphonuclear cells (PMNs) to be attracted to the gastrointestinal tract, adhere, and then be activated. The free radicals are then released and spread systemically, attacking normal tissue through their respiratory burst and causing further tissue injury by releasing intracellular proteases and lipases capable of autodigestion of cellular components. Free radicals also produce arachiodonic acid, leukotrienes, thromboxanes and prostaglandins through lipid peroxidation. The body's natural antioxidant defenses to these free radicals consist principally of glutathione peroxidase, catalase and superoxide dismutase.

Some of the reactions are well known and available agents can be used in combination to either prevent their occurrence or to minimize the adverse affects of the agents produced. The first two abnormalities that occur in the period of ischemia are related to ATP regeneration and xanthine dehydrogenase function.

During normoxia ATP liberates energy for cellular work; in the presence of oxygen, however, ADP combines with hydrogen ion and ATP is re-synthesized. Hypoxanthine combines with $NAD^+$, a reaction catalyzed by xanthine dehydrogenase, to produce xanthine and NADH.

During ischemia, however, ATP degrades beyond ADP to AMP, adenosine, inosine and finally to hypoxanthine. Xanthine dehydrogenase is converted to xanthine oxidase.

During reperfusion which reintroduces oxygen, xanthine oxidase catalyzes the transformation of hypoxanthine to xanthine which also results in the production of superoxide and hydrogen peroxide.

Later reactions produce the hydroxyl radical, superoxide, and hydrogen peroxide which create tissue injury through lipid peroxidation, destruction of protein such as ATPase, destruction of nucleic acids and membrane permeability.

Superoxide, through the process of lipid peroxidation, liberates free fatty acids, particularly arachidonic acid. Arachidonic acid is a substrate for the production of leukotrienes and prostaglandins. Superoxide in the gut also attracts, causes adherence and activation of polymorphonuclear white cells. The hydroxyl radical can also activate PMNS which subsequently liberate proteases and superoxide, the so called respiratory burst, which in the absence of a normal traditional enemy such as bacteria, results in direct tissue injuries, particularly in the pulmonary capillaries. Hydrogen peroxide also combines with superoxide to produce hydroxyl radicals in iron catalyzed reactions such as the Fenton and Haber-Weiss reactions. Thus, free radical production perpetuates further free radical production which leads to a cycle of increasing tissue injury.

$PLA_2$, phospholipase $A_2$, was originally thought only to be important in the process of digestion. However, it has been shown to hydrolyze cell membranes and release free fatty acids which lead to the production of prostaglandins, leukotrienes and lipoxins. It is also involved in generation of highly toxic compounds such as lysophosphatides. Finally, it has been shown to activate PAF which then attracts PMNS to the gut for activation.

During ischemia, intracellular calcium accumulates and has been associated with increasing free radical damage, activiating $PLA_2$, increasing xanthine oxidase activity and decreasing ATP binding. All of these functions accentuate and reinforce the previously mentioned pathways of inducing tissue injury.

Glutamine has been implicated as sustaining mucosal architecture and function, thus preventing gut injury. In addition, glutamine combines with acetyl cysteine to form glutathione. In a reaction catalyzed by the selenium containing enzyme glutathione peroxidase, glutathione is transformed in order to oxidize glutathione which combines with hydrogen peroxide and degrades it to water and prevents hydrogen peroxide to react with superoxide and produce the hydroxyl radical.

To address the problems associated with free radical damage and to decrease hospital stays in patients undergoing elective surgery, the present inventors have developed a composition in unit dosage form to be administered in a therapeutic method of promoting recovery in elective surgery patients.

SUMMARY OF THE INVENTION

The present invention therefore, comprises a micronutrient composition in unit dosage form comprising L-glutamine, N-acetyl-cysteine, vitamin A, vitamin C, vitamin E, folate, magnesium, zinc, selenium and copper for use in therapeutic methods of treatment.

The present invention also relates to a method of treating a treating multiple organ system failure by administering a composition in unit dosage form comprising L-glutamine, N-acetyl-cysteine, vitamin A, vitamin C, vitamin E, folic acid, magnesium, selenium, zinc and copper.

In another embodiment, promoting recovery from an elective surgical procedure comprising administering to a patient in need thereof, prior to said elective surgical procedure and following said elective surgical procedure, as a daily regimen, a composition in unit dosage form comprising L-glutamine, N-acetyl-cysteine, vitamin A, vitamin C, vitamin E, folic acid, magnesium, selenium, zinc and copper.

In a preferred embodiment, at least two unit dosage forms of the inventive composition are administered to a patient in need thereof prior to elective surgery and following elective surgery.

In a particularly preferred embodiment, at least three unit dosage forms of the inventive composition are administered to a patient in need thereof prior to elective surgery and following elective surgery.

Additional objects, features and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENT

The inventive daily regimen was developed by combining agents advocated individually to attack only certain steps in the ischemia-reperfusion process which is associated with elective surgery. The lack of success in earlier reports was related to limited interventions at processes that were repetitive and redundant. By combining these elements, a multi-pronged persistent defense would be created; thus approach might have a better chance of achieving clinical success. Elements that have been demonstrated in clinical and experimental studies to affect ischemia and reperfusion injuries were selected. In addition, many water-soluble agents (Vitamin C, Glutahhione, Selenium, Folate) and fat soluble agents (Vitamin A, E) have been associated as over the counter antioxidant agents to prevent free-radical induced tissue injury. The multi-pronged attack to block the pathways at many steps over time could prevent long term high-morbidity, high-mortality of multiple organ system failure and would represent the best current care available.

To increase global oxygen delivery during reperfusion following elective surgery, isotonic fluids, 5% albumin solutions and red blood cells are administered. In addition to its known effect as an efficient plasma volume expander, albumin is a free radical scavenger which may also prevent increased capillary permeability. Its dual effects are to improve resuscitation and decrease reperfusion injury. In addition to increasing oxygen delivery by inspired oxygen tensions, effort is made to avoid epinephrine and other alpha adrenergic agents which cause splanchnic vasoconstriction. Instead other inotropic and vasodilatory agents are substituted which optimize systemic oxygen delivery as well as counteract splanchnic vasoconstriction. Preferred agents now include isoproterenol, dobutamine, nitroglycerin, nitroprusside, and prostaglandin E. It is contemplated that the present inventive unit dosage form nutrient composition could be used in combination with other drugs administered to patients undergoing elective surgery.

Reperfusion injury can be attenuated by blocking xanthine oxidase and preventing free radical generation with folate or alopurinol and administering free radical scavengers such as mannitol, vitamin C, vitamin A and vitamin E.

Injury related to $PLA_2$ activity may be ameliorated by lidocaine, and steroids, and intracellular calcium content can be decreased by lidocaine which binds calcium in cell membranes. Moreover, lidocaine, vitamin C and vitamin E will stabilize cell membranes and prevent increased capillary permeability which would simplify resuscitation and prevent the accumulation of interstitial edema. Lidocaine has been shown to inhibit the activation of $PLA_2$, to stop activation and cytokine release from eosinophils, macrophages and polymorphonuclear leukocytes (PMNs), block PAF activation and finally to "unprime" PMNs. Lidocaine inhibits respiratory burst of PMNs and has been shown experimentally to attenuate the hemodynamic and inflammatory response to endotoxenia.

In the present invention, glutamine is administered. Glutamine (administered enterally 30 gms QID daily) has been implicated as sustaining mucosal architecture and function by scavenging free radicals and preventing lipid peroxidation. In addition glutamine combines with N-acetyl cysteine (administered enterally 12 gms QID daily) to form glutathione. In the reaction catalyzed by the selenium containing enzyme, glutathione peroxidase, glutathione is transformed to oxidized glutathione. This then combines with hydrogen peroxide and degrades it to water, preventing hydrogen peroxide from reacting with superoxide to produce a hydroxyl radical. N-acetyl cysteine has been reported to favorably affect indirect indicators of tissue oxygenation perhaps because it is a precursor of glutathione. N-acetyl cysteine has been incorporated into a regimen with antioxidants that reduced the mortality rate in human ARDS.

In order for elective surgery patients to recover more rapidly, the physiological mechanism which decreases injury from free radical damage needs to be supplemented by the above recited substances. Therefore, the invention includes a method of promoting recovery by administering a composition containing such substances in a unit dosage form.

Glutamine assists in promoting recovery from elective surgery via direct utilization for fuel as well as indirectly by its anti-catabolic effects. Glutamine is a primary fuel for proliferating fibrobalsts and macrophages. Glutamine is the primary amino acid used by the fibroblasts as an energy source in order to make collagen. Macrophages direct the healing process via release of growth factors. Macrophages depend on glutamine for growth factor production. Due to the increased usage, a glutamine deficiency state can occur rapidly. A unit dosage of the composition according to the method of the present invention may contain between about 8 grams to 15 grams of L-glutamine. In a particularly preferred embodiment, the unit dosage form contains 10 g of L-glutamine. A preferred dosage is between 20 and 30 grams of L-glutamine per day to promote recovery. Thus, at least one unit dosage would be administered per day. It is preferred that two to three unit dosages would be administered per day.

N-acetylcysteine (NAC), a sulfur containing compound containing the amino acid cysteine, is a critical substrate for glutathione GSH synthesis which has direct antioxidant properties and therefore along with glutamine, is a rate limiting factor in GSH production. NAC also appears to have endothelial derived relaxing factor properties, as well as protective properties and may, therefore, improve microvascular blood flow. Cysteine is also a key compound used in many immune defenses, especially the lymphocyte function as well as key sulfur containing proteins. Cysteine deficiency is also well described with severe infection and chronic illness. Cysteine content of standard foods and tube feedings is insufficient to correct a deficiency state. A unit dosage of the composition according to the method of the present invention may contain between about 1 g to about 6 g of N-acetylcysteine. In a particularly preferred embodiment, the unit dosage form contains 4 g of N-acetylcysteine. A preferred total dosage is between about 3 and about 10 g of N-acetylcysteine per day to promote recovery. Thus, at least one unit dosage would be administered per day. It is preferred that two to three unit dosages would be administered per day.

Vitamins are organic substances that are essential in humans for growth and homeostasis. Vitamins are essential nutrients found in very small quantities in the body. Each has a name defined by a letter as well as a chemical name. These compounds play a key role in metabolism, growth and homeostasis and therefore are especially important in surgical critical illness, in which hypermetabolism, healing, and immune function are so important for survival. A deficiency state, which can occur readily, clearly will amplify the magnitude of disease.

Vitamins, in general, are not chemically related and as a result, each has a variety of related functions.

Fat-soluble vitamins (such as A, D, E, K) are absorbed in the intestinal tract with lipids and require bile salts for absorption. These vitamins can be stored, to some degree, so toxicity can occur with excessive use.

The water soluble vitamin, vitamin C, cannot be made by the body and must be consumed from outside sources. Since it has a very short half life (hours), daily consumption of large quantities is required following elective surgery to avoid a deficiency state. The role of vitamin C (ascorbic acid) in the body is very complex, despite its simple structure. It is water soluble, so distribution is in the total body water space. A number of important functions for vitamin C are recognized. The most prominent role is as an antioxidant. Vitamin C is present in plasma and cell cytosol as an antioxidant. Its role is to absorb oxidant vital structures can be altered. The oxidized vitamin C is then excreted. Vitamin C is important in maintaining vitamin E and GSH in its reduced form after oxidation by oxidants. Vitamin C supplementation has a role in promoting elective surgery recovery because of its role in hydroxylation of protein and lysine in collagen strands, which are necessary for collagen cross linking. Ascorbic acid also plays a critical role in fatty and metabolism through carnitine production as well as its role in maintaining neutrophil functions.

Plasma and cell levels of vitamin C have been reported to decrease in elective surgery patients. The decrease in plasma levels correlates with increased plasma lipid peroxides. This deficiency not only increases oxidant injury but also impairs neutrophil function and healing. A unit dosage of the composition according to the present invention may contain between about 500 mg to about 3,000 mg of vitamin C. In a particularly preferred embodiment the unit dosage form contains about 2,000 mg of vitamin C. A preferred dosage is between about 1,000 mg and about 4,000 mg of vitamin C per day to promote recovery. Thus, at least one unit dosage would be administered per day. It is preferred that two to three unit dosages would be administered per day. In addition, doses of over 2 grams parenterally during fluid resuscitation improve hemodynamic stability.

The carotenoids are a fat soluble formula of 40 carbon esters which include β-carotene, a potent antioxidant as well as vitamin A precursor. A portion of exogenous β-carotene will be converted to Vitamin A. In the present inventive composition, the vitamin A is provided in the form of β-carotene.

Vitamin A is a fat soluble multipurpose substance involved promoting recovery from elective surgery. Vitamin A, also known as retinol, is transported on retinol binding protein (RBP). A decrease in RBP, which occurs post injury, will impair retinol delivery to tissues. As opposed to water soluble vitamins, vitamin A is stored in the liver.

β-carotene is a lipid soluble vitamin and precursor which has potent antioxidant activity, similar to Vitamin E, decreasing lipid peroxidation. Deficiency and replacement therapy levels are decreased due to utilization during surgery and lack of replacement. A unit dosage of the composition according to the present invention may contain between about 1,000 IU to about 6,000 IU of vitamin A. In a particularly preferred embodiment, the unit dosage form contains about 4,000 IU of vitamin A. A preferred dosage is between about 3,000 IU and about 10,000 IU of vitamin A per day to promote recovery, assuming that a portion of the β-carotene administered will be converted to Vitamin A. Thus, at least one unit dosage would be administered per day. It is preferred that two to three unit dosages would be administered per day.

The main antioxidant activity function of vitamin E is to avoid cell-membrane damage oxidants. The vitamin E which resides in the fat layer of the cell membrane acts as an antioxidant by becoming oxidized to protect the surrounding membrane lipid. In addition, vitamin E is most important in preventing the lipid peroxidation chain reaction, which can self perpetuate in the absence of vitamin E. A deficiency of vitamin E will lead to a potentiation of oxidant induced cell membrane damage. Oxidized vitamin E is returned to its antioxidant reduced form by cytosol reduced vitamin C and glutathione (GSH) which in turn becomes oxidized. GSH needs to be replaced continuously as it can be lost from the cell once in the oxidized form. Therefore, maintaining adequate cell membrane protection means vitamin E, vitamin C and GSH must be maintained. Vitamin E has also been shown to enhance the immune response. Vitamin E levels decrease after elective surgery due to rapid consumption by the released oxidant and the lack of adequate replacement. Plasma and tissue levels are decreased in 24–48 hours but replacement often lags well behind these losses.

A decrease in vitamin E levels in injured patients corresponds with an increase in plasma lipid peroxides which are markers of oxidant damage. Since vitamin E is fat soluble, parenteral replacement is limited. Administration by the oral route as soon as possible is the optimum approach. A unit dosage of the composition according to the present invention may contain between about 300 IU to about 900 IU of vitamin E. In a particularly preferred embodiment, the unit dosage form contains about 700 IU of vitamin E. A preferred dosage is between about 600 IU and about 1,400 IU of vitamin E per day to promote recovery. Thus, at least one unit dosage would be administered per day. It is preferred that two to three unit dosages would be administered per day.

Folic acid is used in place of allopurinol to block xanthine oxidase. Folate is preferable to allopurinol as a xanthine oxidase blocker because of its widespread use as an antioxidant in standard vitamin supplements and because the dose needed insures a very high therapeutic to toxic dose ratio. The preferred dosage of folic acid is 100–500 μg. Thus, at least one unit dosage would be administered per day. It is preferred that two to three unit dosages would be administered per day.

Magnesium is a macromineral with numerous key roles in metabolism, cell protection and immune function. Key roles include production of ATP through phosphate transfer reactions. In fact, magnesium is a key factor in most adenosine tryphosphate dependent enzyme reactions as well as protein synthesis reactions. Also, the $Na^+$ $K^+$ ATP pumps are magnesium dependent. Additionally, magnesium counteracts the accumulation of intracellular calcium. It also diminishes myocardial ischemia and the incidence of arrythmias.

Magnesium deficiency is extremely common in early post injury and critical illness. Also, hypomagnesemia occurs with refeeding as new cell growth consumes large quantities. A magnesium deficiency state effects cell metabolism, energy production, protein synthesis and immune dysfunction. A unit dosage of the composition according to the present invention may contain between about 100 μg and about 600 μg of magnesium. In a particularly preferred embodiment, the unit dosage form contains about 300 μg of magnesium. A preferred dosage is between about 200 μg and about 600 μg of magnesium per day to promote recovery. Thus, at least one unit dosage would be administered per day. It is preferred that two to three unit dosages would be administered per day.

Micronutrients are essential for cellular function. Micronutrients useful in the present inventive composition include zinc, selenium and copper. They are called nutrients because of their key role in metabolism, but these compounds and elements also are involved in many other aspects of homeostasis, antioxidant protection and immune function. The term micro is used because of the extremely small amounts found in the circulation. Their concentrations are critical to cellular function.

Micronutrients which are inorganic compounds are called trace minerals. The essential trace minerals are utilized and lost in increased quantities with critical illness. Deficiency states therefore can occur easily. Because measurement of adequate levels is difficult, if not impossible, prevention of a deficiency often is accomplished only by increasing intake.

Zinc has been a well studied trace element because of its biologic importance. Zinc is a trace element that can exist in several different states but usually is divalent. The total body amount of zinc is about 1.5 to 3 g. Zinc is moderately well absorbed from the gastrointestinal tract, varying from 14% to 41% complexing which improves absorption. Zinc has an immense number of biologic roles. Zinc is administered in the form of an arginate which increases bioavailability. A unit dosage of the composition according to the present invention may contain between about 3 mg to about 12 mg of zinc. In a particularly preferred embodiment, the unit dosage contains about 10 mg of zinc. A preferred dosage is between about 7 mg and about 20 mg of zinc per day to promote recovery. Thus, at least one unit dosage would be administered per day. It is preferred that two to three unit dosages would be administered per day.

Selenium is present in all tissues in large part due to its critical role in cell glutathione antioxidant protection as a key cofactor for the enzyme glutathione peroxidase. Selenium absorption is in the range of 50 to 100% depending on the carrier. Selenium in addition to its well known role as an antioxidant cofactor plays a role in a number of enzyme systems central to metabolic activity especially in the function of the cytochrome P450 system. Also, selenium is required for thyroid function activity. An increased urinary loss is partially responsible as with most key micronutrients, the deficiency occurs early within several days. A unit dosage of the composition according to the present invention may contain between about 40 μg to about 100 μg of selenium. In a particularly preferred embodiment, the unit dosage form contains about 7 μg of selenium. A preferred dosage is between about 100 μg and about 140 μg of selenium per day to promote recovery. Thus, at least one unit dosage would be administered per day. It is preferred that two to three unit dosages would be administered per day.

Copper (Cu) is widely distributed in human tissues. Although found in micro amounts, this element is a key cofactor for many biologic functions required in critical illness. Copper deficiency is well recognized post-surgery. Also urinary losses are markedly on the increase. The deficiency state is most evident after about 2 weeks post insult. Replacement of Cu rapidly corrects any deficiency. A unit dosage of the composition according to the present invention may contain between about 0.10 mg to about 0.70 mg of copper. In a particularly preferred embodiment, the unit dosage form contains about 0.50 mg of copper. A preferred dosage is between about 0.75 mg and about 1.2 mg of copper per day to promote recovery. Thus, at least one unit dosage would be administered per day. It is preferred that two to three unit dosages would be administered per day.

Accordingly, the present invention attacks the generation of free radicals, provides scavengers, and augments the body's natural defenses in a comprehensive manner. The additional detrimental effects of endotoxin, activated $PLA^2$, activated cytokines and intracellular calcium are also addressed by elements in the care sequence. The adequacy of resuscitation is now judged by a better endpoint, $pH_i$, and therapy has been coordinated to correct persistent intramucosal acidosis.

Methods of Dosing

The dosage administered to patients is guided by a physician skilled in the art on a case by case basis. Patients may receive multiple doses of a composition according to this invention per day depending on the amount the composition needed for the patients' particular condition, nutritional needs, and body size (i.e., body weight, surface area, height, etc.). Where the compositions contain about 10 g glutamine, on average, patients preferably will receive 2 to 4 doses per day but doses can range from 1 dose per day to a much higher level as determined by the patient's physician or health care provider.

A unit dosage form means that the inventive composition is administered in a convenient form, such as, a premeasured lyophilized powder which can be reconstituted and administered to the patient as part of a daily regime. This can be mixed with juice, tea or another form of liquid. The dosage can also be administered by mixing the lyophilized powder into moist food such as applesauce or puddings.

Methods of Manufacture

The claimed composition can be made by methods known to those skilled in the art. The elements comprising the composition are prepared by standard methods of blending and mixing at temperatures and moisture contents which allow blending to take place. The elements comprising the composition are preferably utilized in a dispersable form.

In another embodiment, the claimed composition can be prepared using a standard wet process involving taking the product into a slurry, then processing it through heating it to high temperatures known to those skilled in the art then placing it into a separate chamber where it is blended and granulated.

Methods of Administration

The methods of administration can be either oral dosing or via a feeding tube. For an oral dose at least one unit dosage form is admixed with a beverage or a moist semi-solid food at room temperature. It is recommended that ice cold beverages and liquids be avoided for admixture with the unit dosage of the micronutrient composition. For use with a feeding tube, a unit dosage form of the micronutrient composition is admixed with at least 60 cc of water and infused to a patient via a syringe to a feeding tube. The feeding tube is flushed with additional water and feeding via the tube is continued as per normal use.

Other embodiments of the invention will be apparent to those skilled in the art from consideration of the specification and practice of the invention disclosed herein. It is intended that the specification be considered as exemplary only, with the true scope and spirit of the invention being indicated by the following claims.

As used herein and in the following claims, singular articles such as "a", "an", and "one" are intended to refer to singular or plural.

What is claimed is:

1. A method of promoting recovery from an elective surgical procedure comprising administering to a patient in need thereof, prior to said elective surgical procedure and following said elective surgical procedure, as a daily regimen, a composition in unit dosage form comprising L-glutamine, N-acetyl-cysteine, vitamin A, vitamin C, vitamin E, folic acid, magnesium, selenium, zinc and copper.

2. The method of claim 1, wherein said unit dosage form comprises a pre-measured lyophilized aqueous-soluble rapidly dissolving powder.

3. The method of claim 1, wherein at least two unit dosages are administered to said patient prior to said elective surgical procedure.

4. The method of claim 1, wherein at least three unit dosages are administered to said patient prior to said elective surgical procedure.

5. The method of claim 1, wherein at least two unit dosages are administered to said patient following said elective surgical procedure.

6. The method of claim 1, wherein at least three unit dosages are administered to said patient following said elective surgical procedure.

7. The method of claim 1, wherein said unit dosage form is administered for 1–2 days prior to said elective surgical procedure.

8. The method of claim 1, wherein said unit dosage form is administered for 1–2 days following said elective surgical procedure.

9. The method of claim 1, wherein said unit dosage form is administered for 2 days prior to said elective surgical procedure.

10. The method of claim 1, wherein said unit dosage form is administered for 2 days following said elective surgical procedure.

11. The method of claim 1, wherein said unit dosage form is admixed with a beverage or semi-solid food for oral administration.

12. The method of claim 1, wherein said unit dosage form is adapted for tube-feeding.

13. The method of claim 1, wherein said unit dosage form contains about 7–12 g of L-glutamine.

14. The method of claim 1, wherein said unit dosage form contains about 1–6 g of N-acetyl-N-cysteine.

15. The method of claim 1, wherein said unit dosage form contains about 1,000–6,000 IU of vitamin A.

16. The method of claim 1, wherein said unit dosage form contains about 500–3,000 mg of vitamin C.

17. The method of claim 1, wherein said unit dosage form contains about 300–900 IU of vitamin E.

18. The method of claim 1, wherein said unit dosage form contains about 100–500 µg of folic acid.

19. The method of claim 1, wherein said unit dosage form contains about 100–500 µg of magnesium.

20. The method of claim 1, wherein said unit dosage form contains about 40–100 µg of selenium.

21. The method of claim 1, wherein said unit dosage form contains about 3–12 mg of zinc.

22. The method of claim 1, wherein said unit dosage form contains about 0.1–0.7 mg of copper.

23. The method of claim 1, wherein said unit dosage form comprises about 10 g of L-glutamine, about 4 g of N-acetyl-cysteine, about 4,000 IU of vitamin A, about 2,000 mg of vitamin C, about 700 IU of vitamin E, about 300 µg of folic acid, about 300 µg of magnesium, about 70 µg selenium, about 10 mg of zinc and about 0.5 mg of copper.

24. The method of claim 1, where said unit dosage form is administered in conjunction with another drug useful in the treatment of patients having elective surgery.

25. The method of of claim 1, wherein said unit dosage form contains about 8–15 g of L-glutamine.

26. A method of treating multiple organ system failure comprising administering to a patient in need thereof a composition in unit dosage form comprising L-glutamine, N-acetyl-cysteine, vitamin A, vitamin C, vitamin E, folic acid, magnesium, selenium, zinc and copper.

27. The method of claim 26, wherein said unit dosage form comprises a pre-measured lyophilized aqueous-soluble rapidly dissolving powder.

28. The method of claim 26, wherein at least two unit dosages are administered to said patient.

29. The method of claim 26, wherein at least three unit dosages are administered to said patient.

30. The method of claim 26, wherein said unit dosage form is admixed with a beverage or semi-solid food for oral administration.

31. The method of claim 26, wherein said unit dosage form is adapted for tube-feeding.

32. The method of claim 26, wherein said unit dosage form contains about 7–12 g of L-glutamine.

33. The method of claim 26, wherein said unit dosage form contains about 1–6 g of N-acetyl-N-cysteine.

34. The method of claim 26, wherein said unit dosage form contains about 25,000–6,000 IU of vitamin A.

35. The method of claim 26, wherein said unit dosage form contains about 500–3,000 mg of vitamin C.

36. The method of claim 26, wherein said unit dosage form contains about 300–900 IU of vitamin E.

37. The method of claim 26, wherein said unit dosage form contains about 100–500 µg of folic acid.

38. The method of claim 26, wherein said unit dosage form contains about 100–500 µg of magnesium.

39. The method of claim 26, wherein said unit dosage form contains about 40–100 µg of selenium.

40. The method of claim 26, wherein said unit dosage form contains about 3–12 mg of zinc.

41. The method of claim 26, wherein said unit dosage form contains about 0.1–0.7 mg of copper.

42. The method of claim 26, wherein said unit dosage form comprises about 10 g of L-glutamine, about 4 g of N-acetyl-cysteine, about 4,000 IU of vitamin A, about 2,000 mg of vitamin C, about 700 IU of vitamin E, about 300 µg of folic acid, about 300 µg of magnesium, about 70 µg selenium, about 10 mg of zinc and about 0.5 mg of copper.

43. The method of claim 26, wherein said unit dosage form contains about 8–15 g of L-glutamine.

\* \* \* \* \*